United States Patent [19]
Hill et al.

[11] Patent Number: 5,824,657
[45] Date of Patent: Oct. 20, 1998

[54] AMINOACYL SULFAMIDES FOR THE TREATMENT OF HYPERPROLIFERATIVE DISORDERS

[75] Inventors: Jason M. Hill, Newtonville; Arthur F. Kluge, Lincoln, both of Mass.

[73] Assignee: Cubist Pharmaceuticals, Inc., Cambridge, Mass.

[21] Appl. No.: 820,249

[22] Filed: Mar. 18, 1997

[51] Int. Cl.$^6$ .......................... A61K 31/70; C07H 19/16; C07H 19/167
[52] U.S. Cl. ...................... 514/46; 536/27.23; 536/27.62
[58] Field of Search ........................... 514/46; 536/27.23, 536/27.62

[56] References Cited

U.S. PATENT DOCUMENTS

| | | | |
|---|---|---|---|
| 2,914,525 | 11/1959 | Thomas et al. | 260/211.5 |
| 3,622,561 | 11/1971 | Robins et al. | 260/211.5 |
| 3,817,978 | 6/1974 | Jenkins et al. | 536/4.1 |
| 3,854,480 | 12/1974 | Zaffaroni | 128/260 |
| 3,928,319 | 12/1975 | Jenkins et al. | 536/27.13 |
| 4,452,775 | 6/1984 | Kent | 424/19 |
| 5,039,660 | 8/1991 | Leonard et al. | 514/8 |
| 5,470,967 | 11/1995 | Huie et al. | 536/24.3 |
| 5,594,015 | 1/1997 | Kurtz et al. | 514/369 |

FOREIGN PATENT DOCUMENTS

| | | |
|---|---|---|
| 4215738 A1 | 2/1993 | Germany . |
| 62-056500A2 | 3/1987 | Japan . |
| 62-108896A2 | 5/1987 | Japan . |
| 62-108897 | 5/1987 | Japan . |
| 57206397A2 | 12/1987 | Japan . |
| 63-051398A2 | 3/1988 | Japan . |
| 05060479B | 9/1993 | Japan . |
| 815381 | 6/1959 | United Kingdom . |
| 2284811 | 6/1995 | United Kingdom . |
| 2287464 | 9/1995 | United Kingdom . |
| 9115500 | 10/1991 | WIPO . |

OTHER PUBLICATIONS

Criton et al., "Nucleopeptidic Bioconjugates Containing a Sulfamide Bridge: Linkage Via the Mitsunobu Reaction," *Nucleosides & Nucleotides*, 14(8), 1795–1801 (Oct. 1995).

Huie et al., "Oligonucleotides with a Nuclease–Resistant Sulfur–Based Linkage," *J. Organic Chem.*, 57(17), 4569–4570 (Aug. 14, 1992).

Heacock, D., et al., "Synthesis and Aminoacyl–tRNA Synthetase Inhibitory Activity of Prolyl Adenylate Analogs", *Bioorganic Chemistry*, (1996) 24:273–289. Month of publication data is unavailable.

Sudo, T., et al., "Isolation and Characterization of the Gene Encoding an Aminopeptidase Involved in the Selective Toxicity of Ascamycin Toward *Xanthomonas Campestris* PV. Citri", *Biochem. J.*, (1996), 319:99–102. Month of publication data is unavailable.

Kristinsson, H., et al., "Herbicidally Active Sulfamoyl Nucleosides", *American Chemical Society Symposium Series*, (1995), 584:206–219. (Ch. 19). Month of publication data is unavailable.

Siddiai, S., et al., "Search for New Purine– and Ribose– Modified Adenosine Analogues as Selective Agonists and Antagonists at Adenosine Receptors", *J. Med. Chem.* (1995), 38:1174–1188 (issue No. 7). Month of publication data is unavailable.

Iltzsch, M., et al., "Structure–Activity Relationship for the Binding of Nucleoside Ligands to Adenosine Kinase From *Toxoplasma Gondii*", *Biochemical Pharmacology*, 49:10:1501–1512, (May 17, 1995).

Belrhali, H., et al., "Crystal Structures at 2.5 Angstrom Resolution of Seryl–tRNA Synthetase Complexed With Two Analogs of Seryl Adenylate", *Science*, 263:1432–1436 (Mar. 11, 1994).

Scacchi, A., et al., "Herbicidal Activity of Dealanylascamycin, A Nucleoside Antibiotic", *Pesticide Biochemistry and Physiology*, (1994), 50:149–158. Month of publication data is unavailable.

Ishida, T., et al., "Conformational Features of 5'–O– [N–(L–Alanyl)Sulfamoyl]Adenosine, A Substrate Analogue of Analyl–tRNA Synthetase, Studied by $^1$H–NMR and Energy Calculation Methods", *Chem. Pharm. Bull.*, (1993), 41:5:804–809 (issue No. 5) Month of publication data is unavailable.

Maguire, A., et al., "Synthetic Approaches Towards Nucleocidin and Selected Analogues; Anti–HIV Activity in 4'–Fluorinated Nucleoside Derivatives", *J. Chem. Soc. Perkin. Trans.*, (1993), 1795–1808. Month of publication data is unavailable.

Ueda, H., et al., "X–Ray Crystallographic Conformational Study of 5'–O–[N–(L–Alanyl Sulfamoyl]–Adenosine, A Substrate Analogue for Alanyl–tRNA Synthetase", *Biochimica et Biophysica Acta*, (1991), 126–134. Month of publication data is unavilable.

Suhadolnik, R., et al. "Biosynthesis of the Naturally Ocurring Nucleoside Antibiotics From Adenosine", *Nucleosides & Nucleotides*, 8(5&6), (1989), 983–986. Month of publication data is unavailable.

Take, Y., et al., "Comparative Studies of the Inhibitory Properties of Antibiotics on HIV and AMV Reverse Transcriptases and Cellular DNA Polymerases", *The Journal of Antibiotics*, (1989), 42(1), 107–115. Month of publication data is unavailable.

Ubukata, M., "Chemical Studies on New Antibiotics", *Nippon Nogei Kagaku Kaishi*, (1988), 62(11), 1629–36, (Nov., 1988).

(List continued on next page.)

*Primary Examiner*—John Kight
*Assistant Examiner*—L. Eric Crane
*Attorney, Agent, or Firm*—Wolf, Greenfield & Sacks, P.C.

[57] ABSTRACT

Novel aminoacyl sulfamides are described. These compounds are effective in the treatment of hyperproliferative disorders, specifically psoriasis. Exemplary compounds of this invention are 5'-deoxy-adenosine 5'-N(N-L-phenylalanyl)sulfamide and 5'-deoxy-adenosine 5'-N-(N-L-tryptophanyl)sulfamide.

19 Claims, No Drawings

OTHER PUBLICATIONS

Ubukata, M., et al., "Synthesis and Biological Activity of Aminoacyl Analogs of Ascamycin", *Agric. Biol. Chem.*, 52(5), 1117–1122 (1988). Month of publication data is unavailable.

Castro–Pichel, J., et al., "A Facile Synthesis of Ascamycin and Related Analogues", *Tetrahedron*, (1987), 43:2:383–389. Month of publication data is unavailable.

Osada, H., et al., "Occurrence of an Ascamycin Dealanylating Enzyme, Xc–Amino–Peptidase, in Mammalian Cell Membranes and Susceptibility to Ascamycin", *The Journal of Antibiotics*, 2:286–293 (Feb. 1986).

Rengaraju, S., et al., "5'-O-Sulfamoyladenosine (Defluoronucleocidin From a Streptomyces", *Sci. Reports of Meiji Seika Kaisha*, (1986), 25:49–55. Month of publication data is unavailable.

Ubukata M., et al., "Total Synthesis of Nucleoside Antibiotic, Ascamycin", *Tetrahedron Letters*, (1986), 27:33:3907–3908. Month of publication data is unavailable.

Ubukata M., et al., "Synthesis and Biological Activity of Nucleoside Antibiotics, Ascamycin and its Amino Acid Analogs", *Nucleic Acids Research–Symposium Series No. 16*, (1985), 81–83. Month of publication data is unavailable.

Osada, H., et al., "Mechanism of Action And Selective Toxicity of Ascamycin, A Nucleoside Antibiotic", *Antimicrobial Agents and Chemotherapy*, 27:2:230–233 (Feb. 1985).

Isono, K., et al., "Structure and Biological Activity of Ascamycin, A New Nucleoside Antibiotic", *Nucleic Acids Research–Symposium Series No. 15*, (1984), 65–67. Month of publication data is unavailable.

Isono, K., et al., "Ascamycin and Dealanylascamycin, Nucleoside Antibiotics From Streptomyces" *The Journal of Antibiotics*, 6:670–672 (Jun., 1984).

Alarcon, B., et al., "Screening for New Compounds With Antiherpes Activity", *Antiviral Research*, (1984), 4:231–244. Month of publication data is unavailable.

Takahashi, E., et al., "A New Nucleosidic Antibiotic AT–265", *The Journal of Antibiotics*, (1982), 35(8), 939–947. Month of publication data is unavailable.

Richards, C., "Synthesis of 4'-Methoxyadenosine and Related Compounds", *Carbohydrate Research*, (1982), 100:315–329. Month of publication data is unavailable.

Fukushima, K., et al., "Field Desorption Mass Spectrometry Of Nucleoside Antibiotics", *The Journal of Antibiotics*, 31(4), 377–378 (Apr. 1978).

Gough, G., "New Inhibitors of Platelet Aggregation, 5'-Phosphate, 5'-Phosphorothioate, and 5'-O-Sulfamoyl Derivatives of 2–Substituted Adenosine Analogues", *American Chemical Society*, (1978), 21:6:520–525. Month of publication data is unavailable.

Williamson, J., et al., "Trypanocidal Activity of Antitumor Antibiotics and Other Metabolic Inhibitors", *Antimicrobial Agents and Chemotherapy*, 13(5), 735–744 (May 1978).

Smith, C., et al., "Inhibitors of Hypoxanthine Metabolism In Ehrlich Ascites Tumor Cells in Vitro", *Cancer Treatment Reports*, (1976), 60:10:1567–1584. Month of publication data is unavailable.

Jenkins, I., et al., "4'-Substituted Nucleosides. 2. Synthesis of the Nucleoside Antibiotic Nucleocidin", *Journal of the American Chemical Society*, (1976), 98(11), 3346–3357 (May 26, 1976).

Williamson, J., et al., "Drug–Induced Lesions in Trypanosome Fine Structure: A Guide to Modes of Trypanocidal Action", *Biochemical Pharmacology*, (1975), 24(1), 147–151 (Jan. 1975).

Bacchi, C.J., et al., "Susceptibility of an Insect Leptomonas and *Crithidia Fasciculata* to Several Established Antitrypanosomatid Agents", *Antimicrobial Agents and Chemotherapy*, 6(6),785–790 (Dec. 1974).

Jenkins, I., et al., "Synthesis of the Nucleoside Antibiotic Nucleocidin", *J. Am. Chem. Soc.*, (1971), 93(17):4323–4324. Month of publication data is unavailable.

Bloch, A., et al., "Inhibition of Protein Synthesis by 5'-Sulfamoyladenosine", *Biochemistry*, (1971), 10(24), 4394–4398. Month of publication data is unavailable.

Hoshino, Y., et al., "Effect of Antibiotics on Mycoplasma", *The Journal of Antibiotics*, (1970), 23(11), 531–536. Month of publication data is unavailable.

Jaffe, J., et al., "Trypanocidal Properties of 5'-O-Sulfamoyladenosine, A Close Structural Analog of Nucleocidin", *Experimental Parasitology*, (1970), 28:535–543. Month of publication data is unavailable.

Shuman, D., et al., "The Synthesis of Nucleoside Sulfamates Related to Nucleocidin", *Journal of the American Chemical Society*, 92(11), 3434–3440 (Jun. 3, 1970).

Shuman, D., et al., "The Synthesis of Adenine 5'-O-Sulfamoyl Nucleosides Related to Nucleocidin", *Journal of American Chemical Society*, (1969), 3391–3392, vol. 91, issue No. 12.

Morton, G., et al., "The Structure of Nucleocidin. III (A New Structure)", *Journal of American Chemical Society*, 91(6), 1535–1537 (Mar. 12, 1969).

Chung, S–T., et al., "Studies on ATP Deaminase II. Relationship Between Enzyme Specificity and Substrate Structure", *J. Gen. Appl. Microbiol.*, (1967) 13:237–245. Month of publication data is unavailable.

Florini, J., "Nucleocidin", *Antibiotics (USSR)*, (1967), 427–433. Month of publication data is unavailable.

Florini, J., et al., "Inhibition of Protein Synthesis In Vitro and In Vivo by Nucleocidin, An Antitrypanosomal Antibiotic", *The Journal of Biological Chemistry*, 241(5), 1091–1098 (Mar. 10, 1966).

Sugiura, K., "Chemotherapy of Rous Chicken Sarcoma", *Cancer Chemotherapy Reports*, 22:41–48, (Sep. 1962).

Stephen, L., et al., "The Trypanocidal Activity of Nucleocidin Against *Trypanosoma Vivax* in West African Zebu Cattle", *J. Parasitology*, (1960), 46:509–514. Month of publication data is unavailable.

Waller, C., et al., "The Structure of Nucleocidin", *J. Am. Chem. Soc.*, 79:1011–1012 (Feb. 20, 1957).

Tobie, E., "The Trypanocidal Effect of Nucleocidin In Vivo", *J. Parasitology*, (1957), 43:291–293. Month of publication data is unavailable.

Hewitt, R., et al., "The Activity of a New Antibiotic, Nucleocidin, in Experimental Infections With *Trypanosoma Equiperdum*", (1956–1957), *Antibiotics Annual*, 722–729. Month of publication data is unavailable.

Thomas, S., et al., "Nucleocidin, A New Antibiotic With Activity Against Trypanosomes", *Antibiotics Annual*, (1956–1957), 716–721. Month of publication data is unavailable.

Pope, A., et al., "The Kinetic Mechanism of Substrate and Inhibitor . . . Kinetics" Poster Presented at the Keystone Symposia on Molecular and Cellular Biology, Taos, New Mexico, Feb. 1–6, (1997).

AMINOACYL SULFAMIDES FOR THE TREATMENT OF HYPERPROLIFERATIVE DISORDERS

FIELD OF THE INVENTION

The present invention relates to methods and pharmaceutical compositions for use in the treatment of hyperproliferative disorders, such as the excessive proliferation of skin cells caused by psoriasis. More particularly it relates to compositions containing aminoacyl-tRNA synthetase inhibitors.

BACKGROUND OF THE INVENTION

Psoriasis is a chronic skin disease most commonly characterized as inflamed swollen skin lesions covered with silvery white scales. This type of psoriasis is known as plaque psoriasis or psoriasis vulgaris. Other types of psoriasis display characteristics such as weeping, pus-like blisters (pustular psoriasis), severe sloughing of the skin (erythrodermic psoriasis), drop-like dots (guttate psoriasis) and smooth inflamed legions (inverse psoriasis). The degree of severity of psoriasis is commonly referred to as mild (affecting less than 5% of the body's surface), moderate (affecting 5–30% of the body's surface) and severe (affecting greater than 30% of the body's surface). The type and severity of the disease varies from individual to individual and may also vary within an individual.

Psoriasis affects millions of people worldwide: men and women, young and old. It can be disabling and disfiguring and in severe cases is responsible for hundreds of deaths each year. Additionally, people afflicted with psoriasis are often plagued by emotional distress such as embarrassment, frustration, fear and depression. It is unknown what exactly causes psoriasis, although it is known that hyperproliferation of the skin cells is occurring.

Skin cells have two growth patterns, normal and wound healing. In a normal growth pattern dead skin cells are shed from the skin at the same rate as new cells are formed, maintaining a balance. The time period from cell birth to cell death is about 28 days. In a wound healing growth pattern the skin cells are formed at an elevated rate, presumably to repair the wound. This process is accompanied by inflammation and an increase in blood supply at the wound site.

Psoriatic skin is characteristic of cell growth in the wound healing growth pattern, however, there is no wound. The time between cell birth and cell death can be as little as 2–4 days. The skin cannot shed the dead cells fast enough so the excessive skin cells build up and form the elevated scaly lesions. The increased blood supply to the area is responsible for the redness of the lesion.

Various treatments for psoriasis are available, however, no psoriasis therapy is universally effective, alone or combined. These treatments are generally temporary and they work with varying degrees of success. They can be cosmetically unpleasant and pose additional health threats.

Systemic drug therapies can have serious side effects on organ functions. Methotrexate, for example, has been associated with liver cirrhosis and fibrosis. Retinoids are teratogens and are therefore not recommended for use in women of child bearing age. These drugs have also been associated with eye and lip inflammation, nose bleeds, bone spurs and hair loss. Cyclosporine has been implicated to have an adverse effect on blood pressure and kidney function.

Ultraviolet light therapies are generally used only in severe cases of psoriasis. These therapies have been associated with premature aging of the skin and some skin cancers. In some cases nausea, itching and redness can also result.

Topical therapies are not without adverse effects. Anthralin can burn normal appearing skin surrounding lesions. Coal tars can make skin more sensitive to sunlight. Corticosteroids if overused can cause the skin to thin and resistance to these medications can sometimes develop. Calcipotriene has been shown to cause side effects among older patients and is not recommended for women of child bearing age.

Novel compounds which can inhibit the growth of hyperproliferative cells have potential as useful therapeutic agents to treat psoriasis. Because of the seriousness of psoriasis and the lack of adequate therapies, there is a need for alternative therapeutic approaches to treating this hyperproliferative disorder.

SUMMARY OF THE INVENTION

Aminoacyl tRNA synthetases (aaRS) are a family of essential enzymes that are found in virtually every biological cell and are one of the factors responsible for maintaining the fidelity of protein synthesis. They specifically catalyze the aminoacylation of tRNA in a two step reaction:

amino acid (AA)+ATP=>AA-AMP+PPi AA-AMP+tRNA= >tRNA-AA+AMP

The enzyme binds adenosine triphosphate (ATP) and its specific amino acid to catalyze formation of an aminoacyl adenylate intermediate (AA–AMP) with concomitant release of pyrophosphate (PPi). In the second step, the amino acid is transferred to the 2' or 3' terminus of the tRNA yielding "charged" tRNA and adenosine monophosphate (AMP). The charged tRNA delivers the amino acid to the ribosome to be added to the nascent polypeptide chain on the ribosome.

Generally, there are at least twenty essential enzymes in this family for most organisms. Inhibition of any of the essential tRNA synthetases disrupts protein translation, ultimately resulting in growth inhibition. Pseudomonic acid A, an antibacterial agent currently used in human therapy, provides clear evidence of the utility of tRNA synthetase inhibitors as useful pharmaceuticals. Pseudomonic acid A binds to isoleucyl-tRNA synthetase, and inhibits isoleucyl adenylate formation in several Gram positive bacterial pathogens such as *Staphylococcus aureus*, resulting in the inhibition of protein synthesis, followed by growth inhibition.

The present invention relates to novel compounds which inhibit aminoacyl tRNA synthetases. The working examples demonstrate that these compounds are useful in the treatment of psoriasis. Described herein are twenty compounds which inhibit aminoacyl tRNA synthetases.

The present invention comprises, in a first aspect, compounds of Formula I

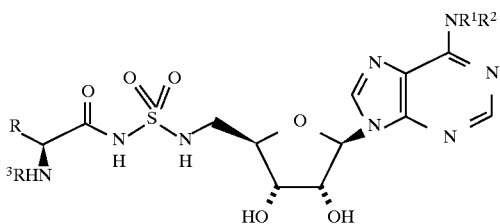

wherein substituent R is selected from hydrido, alkyl, cycloalkyl, aryl and arylalkyl groups.

Each of substituents $R^1$ and $R^2$ is independently selected from hydrido, alkyl, aryl and arylalkyl.

Substituent $R^3$ is hydrido, or alternatively, R and $R^3$ can together form a pyrrolidine ring.

Pharmaceutically-acceptable salts of compounds of Formula I are also covered by this invention.

Preferably, R is hydrido, alkyl or arylalkyl, more preferably, arylalkyl, even more preferably, benzyl or 3-indolylmethyl. Preferably, each of $R^1$, $R^2$, and $R^3$ is independently hydrido. In preferred forms of this aspect of the invention any one or more groups from which the substituents R, $R^1$, $R^2$ and $R^3$ are selected can be omitted, provided that said lists each include at least one such substituent group.

Another aspect of the invention comprises a method of inhibiting an aminoacyl tRNA synthetase using the compound(s) of Formula I.

Another aspect of the invention is to provide a pharmaceutical composition comprising the compounds of Formula I, useful in the treatment of psoriasis. These compositions can also be used to treat other hyperproliferative disorders such as cancer. A related aspect of the invention provides a method of making a medicament which involves placing a compound in accordance with the first aspect of the invention in a suitable pharmaceutically-acceptable carrier.

Yet another aspect of the invention is to provide a method of treating hyperproliferative disorders using the pharmaceutical compositions of the present invention.

A further aspect of the invention comprises using the compounds of Formula I as positive controls in assays which screen for tRNA synthetase inhibitors.

DETAILED DESCRIPTION OF THE INVENTION

I. Definitions

Molecular terms, when used in this application, have their common meaning unless otherwise specified. The term "hydrido" denotes a single hydrogen atom. The term "amino" denotes a nitrogen atom containing two substituents independently selected from hydrido, alkyl, cycloalkyl, aryl, acyl, carboxyamido or carboalkoxy groups, wherein the substituent can be the same or different. The term "carboalkoxy" denotes a carbonyl radical adjacent to an alkoxy or aryloxy group. The term "carboxyamido" denotes a carbonyl radical adjacent to an amino group. The term "thio" denotes a divalent sulfur atom containing a substituent selected from hydrido, alkyl, cycloalkyl, or aryl group, such as, methylthio and phenylthio.

Alkyl groups can be linear or branched, saturated or unsaturated, and have up to about ten. carbon atoms. One or more hydrogen atoms can also be replaced by a substitutent group selected from acyl, amino, carboalkoxy, carboxy, carboxyamido, cyano, halo, hydroxy, nitro, thio, alkyl, cycloalkyl, alkoxy, aryloxy, sulfoxy, and guanido groups. Preferred alkyl groups are "lower alkyl" groups having one to about four carbon atoms. Equally preferred alkyl groups are unsubstituted or include amino, carboxy, carboxyamido, hydroxy, thio and guanido groups. More preferred alkyl groups are methyl, isopropyl, isobutyl, 1-methylpropyl, thiomethylethyl, hydroxymethyl, 1-hydroxyethyl, thiomethyl, carboxyamidomethyl, carboxyamidoethyl, carboxymethyl, carboxyethyl, aminobutyl and guanido.

Aryl groups can contain zero to four hetero atoms selected from oxygen, nitrogen and sulfur in a single or fused carbocyclic or heterocyclic ring system, having from five to fifteen ring members. One or more hydrogen atoms may also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. One or more hydrogen atoms may also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together may form a fused cycloalkyl ring. Examples of a cycloalkyl group include cyclopropyl, cyclobutyl, cyclohexyl, cycloheptyl, morpholinyl, piperidinyl, and pyrrolidinyl. An alkoxy group denotes an oxygen atom substituted with an acyl, alkyl or cycloalkyl group. Examples include methoxy, tert-butoxy, benzyloxy, and cyclohexyloxy. An aryloxy group denotes an oxygen atom substituted with an aryl group. Examples of aryloxy groups are phenoxy, 4-carbobenzyloxyphenoxy, 4-phenoxyphenoxy. Sulfoxy groups comprise a hexavalent sulfur atom bound to two or three substituents selected from the group consisting of oxo, alkyl, aryl and cycloalkyl groups, wherein at least one of said substituents is oxo.

The pharmaceutically-acceptable salts of the compounds of Formula I include acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of Formula I may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of Formula I include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine and procaine. All of these salts may be prepared by conventional means from the corresponding compound of Formula I by treating, for example, the compound of Formula I with the appropriate acid or base.

The compounds of Formula I have centers of asymmetry as indicated by the wedge-shaped and dashed lines. Bonds that extend above the plane of the paper (β bonds) are depicted by darkened wedge-shaped lines, whereas, bonds extending below the plane of the paper are shown as dashed lines. The absolute configuration of these centers is indicated by the stereochemical descriptors R and S, this R and S notation corresponding to the rules described in *Pure Appl. Chem.*, 45, 11–30, (1976). The compounds of this invention may have chiral centers in addition to those indicated. Unless otherwise indicated, the chemical designation of compounds denotes the mixture of all possible stereochemical isomeric forms.

The compounds of Formula I are thus capable of existing in the form of optical isomers as well as in the form of racemic or non-racemic mixtures thereof. The compounds of Formula I can be utilized in the present invention as a single diastereomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula I can likewise be obtained by utilizing optically active starting materials. These isomers may be in the form of a free acid, a free base, an ester or a salt.

The invention also embraces isolated compounds. An isolated compound refers to a compound which represents at least 10% of the compound present in the mixture and exhibits a detectable (i.e. statistically significant) biological activity when tested in conventional biological assays such as those described herein.

II. Description

According to one aspect of the invention, compounds of Formula I are provided. The compounds are useful for inhibiting the enzymatic activity of aminoacyl-tRNA synthetases. The compounds are particularly potent inhibitors of cell proliferation.

A preferred class of compounds of Formula I are compounds in which R is hydrido, alkyl or arylalkyl. Exemplary alkyl and arylalkyl compounds are provided in the definitions.

A further preferred class of compounds of Formula I are compounds in which R is arylalkyl.

A more preferred class of compounds of Formula I are compounds in which R is benzyl or 3-indolylmethyl.

An even more preferred class of compounds of Formula I are compounds in which R is benzyl or 3-indolylmethyl and each of $R^1$, $R^2$ and $R^3$ is hydrido.

Specific compounds most preferred are 5'-deoxyadenosine 5'-N-(N-L-phenylalanyl)sulfamide and 5'-deoxyadenosine 5'-N-(N-L-tryptophanyl)sulfamide.

The compounds of the present invention are active against a variety of hyperproliferative disorders including, for example, psoriasis and cancer.

The phrase "therapeutically-effective amount" means that amount of a compound of Formula I which prevents the onset of, alleviates the symptoms of, or stops the progression of a disorder or disease which is, at least in part, the result of hyperproliferation of cells. A "hyperproliferative disorder" is a condition that is characterized by excessive cell proliferation. "Excessive", with respect to cell proliferation, refers to an amount of cell proliferation which is (1) greater than the amount of proliferation that occurs in a normal, healthy subject, and (2) results in an adverse medical condition. The term "treating" is defined as administering, to a subject, a therapeutically-effective amount of a compound of Formula I. The term "subject", as described herein, is defined as a mammal.

In a second aspect, the invention provides a pharmaceutical composition comprising a compound of the invention, preferably a compound in accordance with the first aspect of the invention, and a pharmaceutically-acceptable carrier. A related aspect of the invention provides a method of making a medicament which involves placing a compound in accordance with the first aspect of the invention in a suitable pharmaceutically-acceptable carrier. Preferably, the pharmaceutically acceptable carrier is suitable for topical administration.

According to another aspect of the invention, a method for inhibiting an aminoacyl-tRNA synthetase is provided which comprises contacting an aminoacyl-tRNA synthetase with a compound of Formula I under the same types of conditions in which the aminoacyl-tRNA synthetase would interact with its natural substrate to form an aminoacyl adenylate intermediate and, preferably to further form a charged tRNA. Such conditions are known to those skilled in the art (see also e.g., the Examples for conditions). This method involves contacting an aminoacyl-tRNA synthetase with an amount of compound of Formula I that is sufficient to result in detectable aminoacyl-tRNA synthetase inhibition. The aminoacyl tRNA synthetase can be contacted with the compounds of Formula I in vivo or in vitro. This method is used in vivo, for example, for treating hyperproliferative disorders in mammals. Alternatively, the method is used in vitro, for example, as positive controls in assays to identify aminoacyl-tRNA synthetase inhibitors (vide infra).

In accordance with another aspect of the invention, the compositions disclosed herein are used for treating a subject afflicted by or susceptible to a hyperproliferative disorder. Preferred subjects of the present invention have only one type of hypeproliferative disorder. More preferably, subjects of the present invention have psoriasis and do not have any other hyperproliferative disorder. The method involves administering to the subject a therapeutically-effective amount of the compound of Formula I. According to this aspect of the invention, the novel compositions disclosed herein are placed in a pharmaceutically-acceptable carrier and are delivered to a recipient subject (preferably a human) in accordance with known methods of drug delivery. The compounds of the present invention may be administered alone or in combination with one or more agents known for treating a hyperproliferative disorder. Typical antipsoriasis agents include methotrexate, retinoids, cyclosporine, anthralin, coal tars, corticosteroids, calcipotriene and PUVA and UVB light therapies. Exemplary procedures for delivering an antipsoriasis agent are described in U.S. Pat. No. 5,594,015 issued to Kurtz et al., the entire contents of which is incorporated in its entirety herein by reference. In general, the methods of the invention for delivering the compositions of Formula I in vivo utilize art-recognized protocols for delivering the agent with the only substantial procedural modification being the substitution of the compounds of Formula I for the drugs in the art-recognized protocols.

The pharmaceutical preparations disclosed herein are prepared in accordance with standard procedures and are administered at dosages that are selected to reduce, prevent or eliminate the condition (See, e.g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antihyperproliferative agents for human therapy). The compositions of Formula I can be delivered using controlled or sustained release delivery systems (e.g., capsules, bioerodable matrices). Exemplary delayed release delivery systems for drug delivery that would be suitable for administration of the compositions of Formula I are described in U.S. Pat. Nos. 4,452,775 (issued to Kent), 5,039,660 (issued to Leonard), 3,854,480 (issued to Zaffaroni).

The pharmaceutically-acceptable compositions of the present invention comprise one or more compounds of Formula I in association with one or more nontoxic, pharmaceutically-acceptable carriers and/or diluents and/or adjuvants and/or excipients, collectively referred to herein as "carrier" materials, and if desired other active ingredients.

The compounds of the present invention may be administered by any route, preferably in the form of a pharmaceutical composition adapted to such a route, and would be dependent on the condition being treated. The compounds and compositions may, for example, be administered orally, intravascularly, intraperitoneally, subcutaneously, intramuscularly or topically. The preferred method of administration is topical administration.

For oral administration, the pharmaceutical compositions may be in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, nonaqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions may also be administered via injection. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers.

For topical use the compounds of the present invention may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil in water or water in oil emulsions using mineral oils, petrolatum and the like, as well as gels such as hydrogel. Alternative topical formulations include shampoo preparations, oral pastes and mouthwash.

For application to the eyes or ears, the compounds of the present invention may be presented in liquid or semi-liquid form formulated in hydrophobic or hydrophilic bases as ointments, creams, lotions, paints or powders.

For rectal administration the compounds of the present invention may be administered in the form of suppositories admixed with conventional carriers such as cocoa butter, wax or other glyceride.

Alternatively, the compounds of the present invention may be in powder form for reconstitution at the time of delivery.

The dosage regimen for treating a hyperproliferative disorder with the compound and/or compositions of this invention is selected in accordance with a variety of factors, including the type, age, weight, sex and medical condition of the patient, the severity of the hyperproliferative disorder, the route and frequency of administration and the particular compound employed. In general, dosages are determined in accordance with standard practice for optimizing the correct dosage for treating a hyperproliferative disorder.

The compositions may contain from 0.01% to 99% by weight of the active ingredient, depending on the method of administration. A preferred method of practicing the invention is to apply the compound(s) of Formula I in a cream or oil based carrier directly to the psoriatic skin. A dosage range for topical treatment is preferably 0.01% to about 10% (weight/volume) in a cream. Typically this cream is applied twice a day. Alternatively an aerosol can be used topically. A shampoo may be used for topical administration to the scalp.

In a further aspect of the invention, compounds of Formula I are useful as positive controls in an in vitro method of screening for inhibitors of aminoacyl-tRNA synthetase activity. In this assay, the inhibitory effect of a compound of unknown inhibitory activity is assessed by monitoring aminoacyl-tRNA synthetase activity according to standard techniques. For example, an aaRS enzyme is maintained under conditions suitable for aminoacyl-adenylate formation, the enzyme is contacted with the compound to be tested, and formation of the aminoacyl-adenylate is monitored by standard assay. A reduction in the activity measured in the presence of the compound, as compared with the activity in the absence of compound, is indicative of inhibition of aminoacyl-tRNA synthetase activity by the compound. In an effort to insure the integrity of the assay, a parallel assay is conducted in which the inhibitory activity of a compound of Formula I is assessed. Since the compounds of Formula I which are shown in Table I are known inhibitors of aminoacyl-tRNA synthetases, they serve as positive controls for the assay of compounds of unknown inhibitory activity. The absence of inhibition in an assay using a compound of Formula I is indicative of a problem in the assay itself.

Further references to features and aspects of the invention are provided in the Claims and Examples set out hereafter.

GENERAL SYNTHETIC PROCEDURES

General Procedure I

Compound 1, prepared from commercially available adenosine via the procedure disclosed in M. Kolb et al., *J. Med. Chem.*, 25, 550–556 (1982), is converted to compound 2 by treatment with sulfamoyl chloride and a base such as sodium hydride, triethylamine, diazabicycloundecene, dibutyltin oxide or caesium carbonate in an appropriate solvent such as tetrahydrofuran, dichloromethane or acetonitrile at temperatures ranging from 0° C. to ambient.

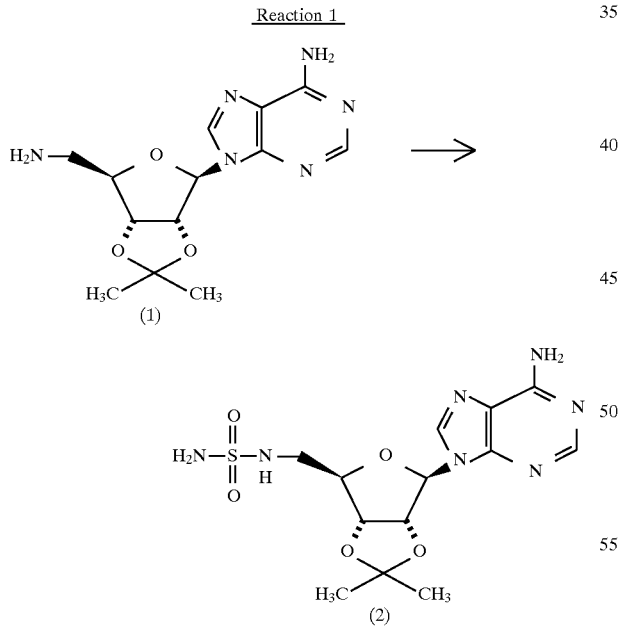

Alternatively compound 1 is converted to compound 3 by treatment with N-carbobenzyloxysulfamoyl chloride and a base such as triethylamine, 4-methylmorpholine, diazabicycloundecene or caesium carbonate in an appropriate solvent such as tetrahydrofuran, dichloromethane or acetonitrile at temperatures ranging from 0° C. to ambient.

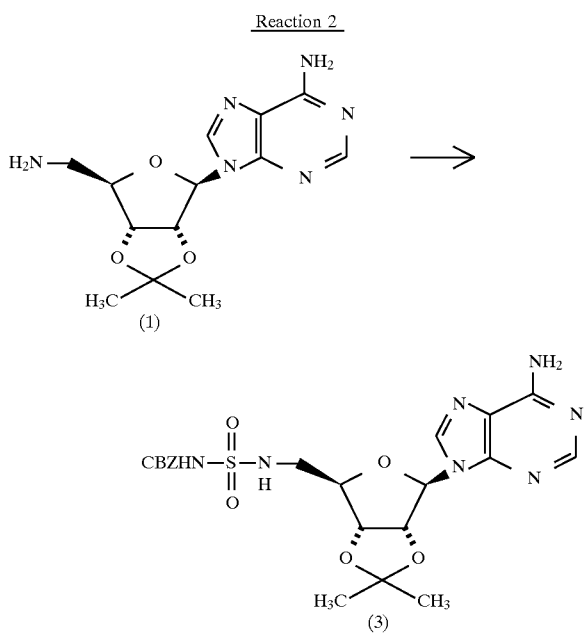

wherein CBZ is defined as carbobenzyloxy.

Compound 3 is converted to compound 2 by treatment with A and hydrogen gas at 1–4 atmospheres in an appropriate solvent such as ethanol, methanol or acetic acid at ambient temperature.

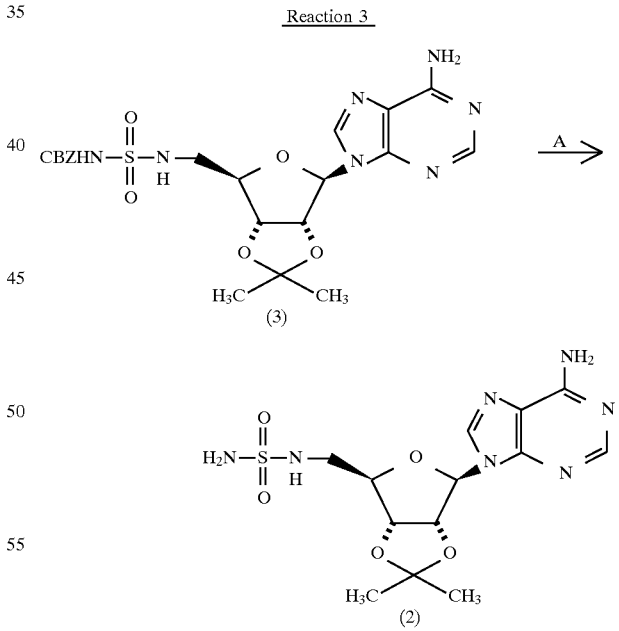

wherein A is a metal catalyst such as palladium on carbon or platinum oxide.

Compound 2 is converted to compound 4 by treatment with compound 5, B and C in an appropriate solvent such as dichloromethane, tetrahydrofuran or dimethylformamide at temperatures ranging from −25° C. to 40° C.

Reaction 4

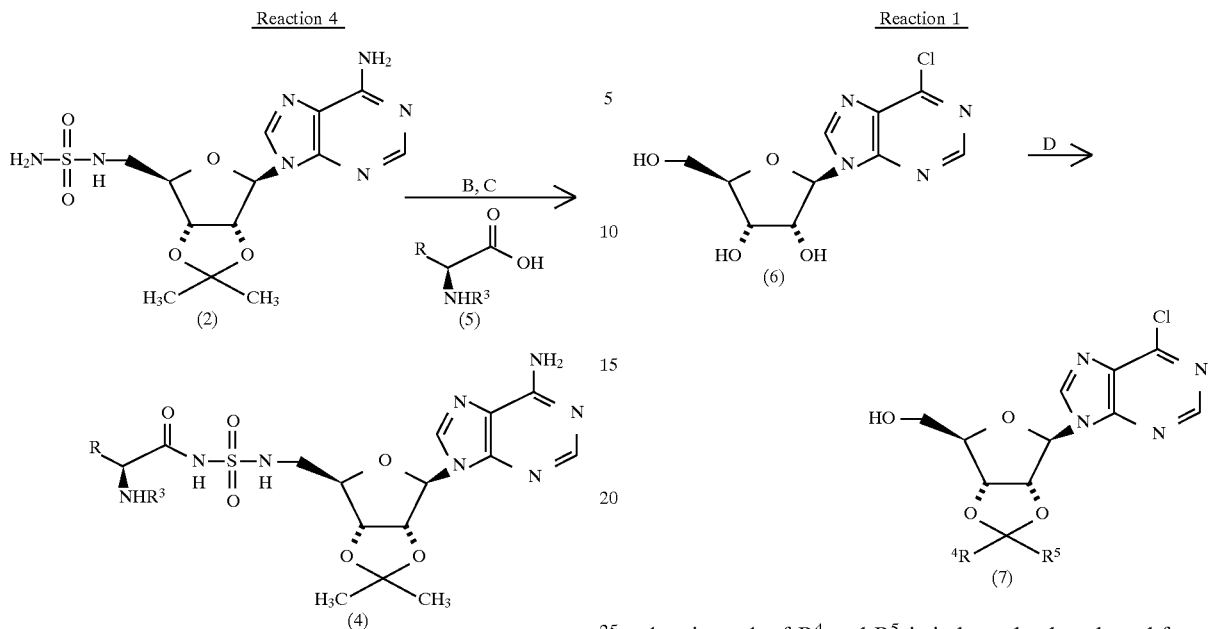

wherein R and $R^3$ are as previously defined; wherein B is a dehydrating agent such as dicyclohexylcarbodiimide, ethyl-3-(3-dimethylaminopropyl)carbodiimide or carbonyldiimidazole; wherein C is an acylation catalyst such as 4-dimethylaminopyridine.

Compounds of Formula I are obtained by deprotection of compound 4 according to standard procedures known to those skilled in the art (See e.g. Protective Groups in Organic Chemistry, 2nd Edition, T. W. Greene, P. G. M. Wuts, Wiley Interscience, New York, 1991, the contents of which are incorporated by reference, for a general description of the methods for deprotecting protecting groups). Typically compound 4 is treated in one of the three following ways:

Treatment 1) Compound 4 is treated with trifluoroacetic acid and water (5:2) at temperatures ranging from 0° C. to 70° C. or,
Treatment 2) Compound 4 is treated as described in Treatment 1 above then treated with A (vide supra) and hydrogen gas at 1–4 atmospheres in an appropriate solvent such as ethanol, methanol or acetic acid at temperatures ranging from ambient to 50° C., or
Treatment 3) Compound 4 is first treated with A as described in Treatment 2 above then treated as per Treatment 1 above.

General Procedure 2

Commercially available compound 6 (Aldrich Chemical Company, Milwaukee, Wis.) is converted to compound 7 by treatment with D in the presence of an acid such as sulfuric acid, perchloric acid, 4-toluenesulfonic acid, camphorsulfonic acid, or copper (II) sulfate in an appropriate solvent such as acetone, diethyl ether or toluene at temperatures ranging from 0° C to the boiling point of the solvent.

wherein each of $R^4$ and $R^5$ is independantly selected from hydrido, alkyl, aryl or cycloalkyl; wherein D is an aldehyde or ketone containing $R^4$ and $R^5$ or their synthetic equivalents, such as 2,2-dimethoxypropane or 2-methoxypropene.

Compound 7 is converted to compound 8 by treatment with an amine in an appropriate solvent such as dimethylformamide, dimethyl sulfoxide, water or toluene at temperatures ranging from 0° C. to the boiling point of the solvent.

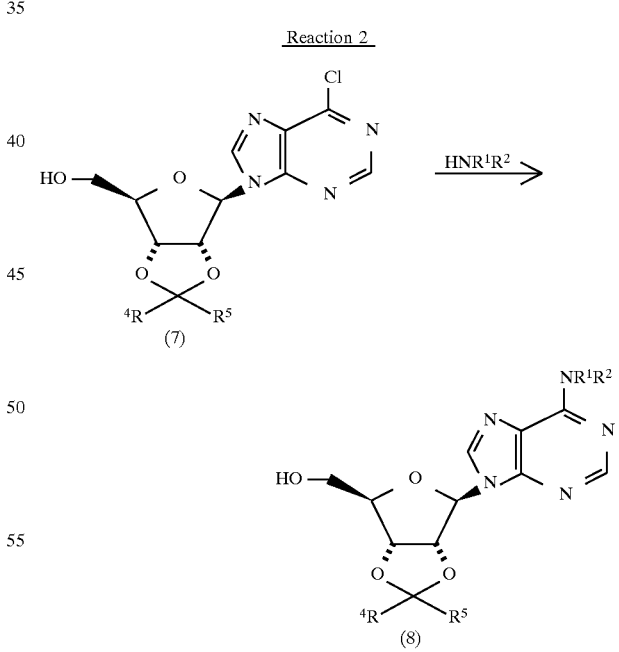

wherein $R^1$, $R^2$, $R^4$ and $R^5$ are as previously defined.

Compound 8 is converted to compound 9 by treatment with E and, if appropriate, a base such as triethylamine, 4-methylmorpholine, diazabicycloundecene, imidazole, or diisopropylethylamine in an appropriate solvent such as dichloromethane, tetrahydrofuran, diethyl ether or acetonitrile at temperatures ranging from 0° C. to ambient.

Reaction 3

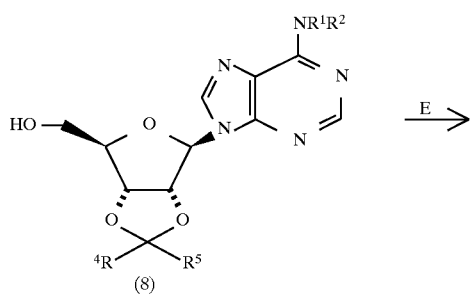

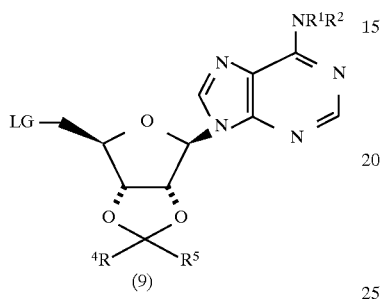

wherein $R^1$, $R^2$, $R^4$ and $R^5$ are as previously defined; wherein LG is a leaving group such as triflate, halogen, tosylate or mesylate; wherein E is a reagent capable of converting a hydroxy group into a leaving group such as methanesulfonyl chloride, 4-toluenesulfonyl chloride, triphenyl phosphine/carbon tetrabromide, triphenyl phosphine/iodine.

Compound 9 is converted to compound 10 by treatment with F in an appropriate solvent such as tetrahydrofuran, dimethylformamide, dimethyl sulfoxide or toluene at temperatures ranging from ambient to 80° C.

Reaction 4

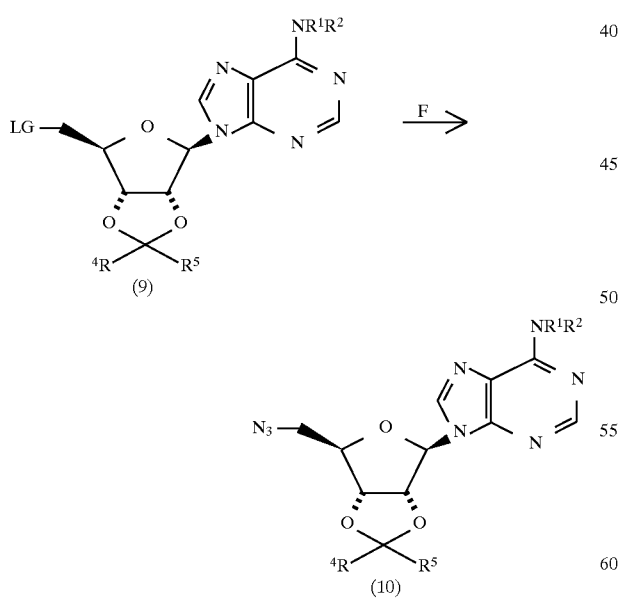

wherein $R^1$, $R^2$, $R^4$, $R^5$ and LG are as previously defined; wherein F is a reagent capable of displacing a leaving group with azide such as lithium azide or sodium azide.

Compound 10 is converted to compound 11 by treatment with A and hydrogen gas at 1–4 atmospheres in an appropriate solvent such as ethanol, methanol or acetic acid at ambient temperature.

Reaction 5

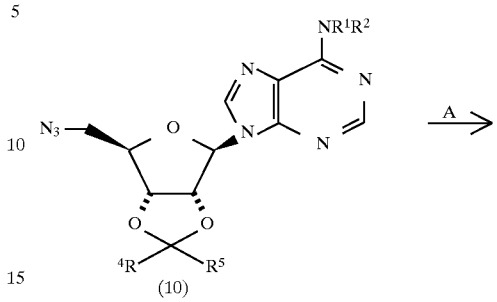

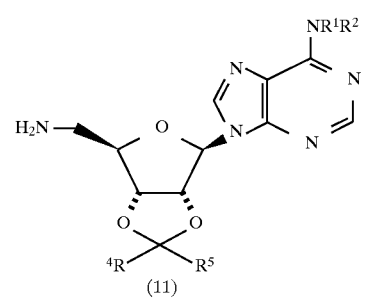

wherein $R^1$, $R^2$, $R^4$ and $R^5$ and A are as previously defined.

Compound 11 is converted to compound 12 by treatment with sulfamoyl chloride according to Reaction 1 of General Procedure 1 or by treatment with N-carbobenzyloxysulfamoyl chloride according to Reaction 2 of General Procedure 1 followed by treatment with A according to Reaction 3 of General Procedure 1.

Reaction 6

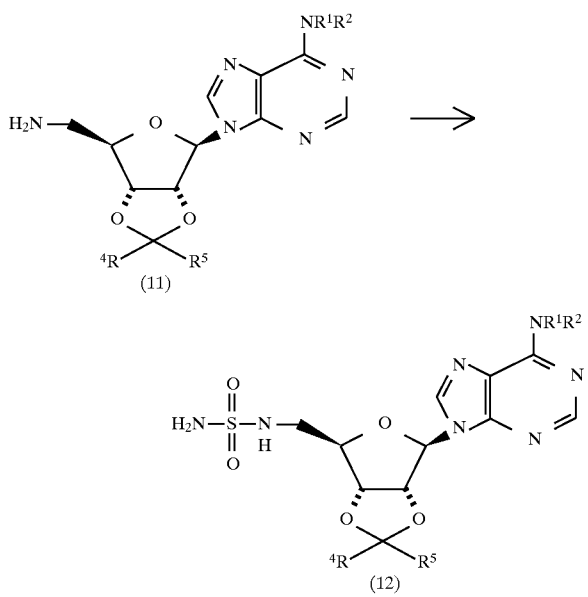

wherein $R^1$, $R^2$, $R^4$ and $R^5$ and A are as previously defined.

Compound 12 is converted to compound 13 by treatment with compound 5, B and C according to Reaction 4 of General Procedure 1

Reaction 7

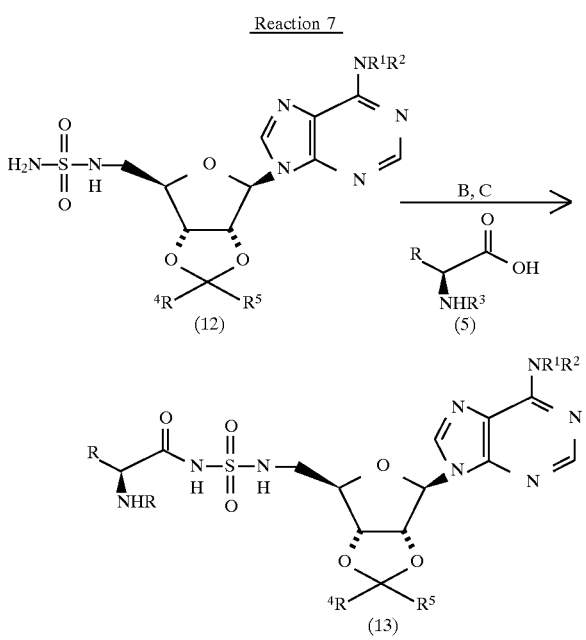

wherein $R^1$, $R^2$, $R^4$, $R^5$, B and C are as previously defined. Compound 13 may be fully deprotected according to the standard procedures that apply to compound 4 in General Procedure 1.

The preparation of representative compounds of Formula I is described in detail in Examples 1–4, below. Table I is a list of specific examples within Formula I.

EXAMPLES

The following Examples 1–4 are detailed descriptions of the methods of preparation of compounds of Formula I. These detailed preparations fall within the scope of, and serve to exemplify, the above described General Procedures which form part of the invention. These Examples 1–4 are presented for illustrative purposes only and are not intended as a limitation on the scope of the invention.

Example 1

Preparation of 5'-deoxy-6-N-phenyl-adenosine 5'-N-(N-L-phenylalanyl)sulfamide

To a slurry of 6-chloropurine riboside (5.015 g) in acetone (100 ml) was added 2,2-dimethoxypropane (10 ml) and 10-camphorsulfonic acid (100 mg). The mixture was stirred at room temperature for 1 day. The mixture was diluted with ethyl acetate (500 ml) washed with saturated sodium chloride (2×200 ml) and dried over anhydrous magnesium sulfate. Evaporation gave a white solid which was purified by silica gel chromatography (1:1 ethylacetate hexanes) to give 6-chloro-2',3'-O-(1-methylethylidene)purine riboside as a white crystalline solid (5.06 g)

6-chloro-2',3'-O-(1-methylethylidene)purine riboside (972 mg) and aniline (1.08 ml) in dry dimethylformamide (8 ml) were heated to 90° C. under an atmosphere of nitrogen for 16 hours. The mixture was then poured into ethylacetate (200 ml) washed with water (2×100 ml) dried over anhydrous magnesium sulfate and evaporated to a brown oil. The oil was purified by silica gel chromatography (30–50% ethylacetate in hexanes) to yield 2',3'-O-(1-methylethylidene)-6-N-phenyl adenosine as a brown foam (757 mg).

To a solution of 2',3'-O-(1-methylethylidene)-6-N-phenyl adenosine (757 mg) in dry dichloromethane (30 ml) was added triethylamine (550 μl) and the mixture cooled to 0° C. Methanesulfonyl chloride (168 μl) was added dropwise to the mixture and after 2 hours at 0° C. the mixture was allowed to warm to room temperature and an additional (100 μl) of methanesulfonyl chloride was added. After 30 minutes the mixture was diluted with dichloromethane (100 ml), washed with water (2×50 ml) dried over anhydrous magnesium sulfate and evaporated to a brown foam. Purification by silica gel chromatography (40–50% ethylacetate in hexanes) gave 5'-O-methanesulfoxy-2',3'-O-(1-methylethyloidene)-6-N-phenyl adenosine (759 mg) as a light brown foam.

To a solution of 5'-O-methanesulfoxy-2',3'-O-(1-methylethylidene)-6-N-phenyl adenosine (759 mg) in dry dimethylformamide (15 ml) was added sodium azide (0.5 g) and the mixture heated to 80° C. under an atmosphere of nitrogen for 4 hours. The mixture was allowed to cool to room temperature before being poured into ethylacetate (150 ml), washed with water (3×100 ml), dried over anhydrous magnesium sulfate and evaporated to a brown oil. Purification by silica gel chromatography (25% ethylacetate in hexanes) gave 5'-azido-5'-deoxy-2',3'-O-(1-methylethylidene)-6-N-phenyl adenosine (483 mg) as a colorless foam.

5'-azido-5'-deoxy-2',3'-O-(1-methylethylidene)-6-N-phenyl adenosine (483 mg) in methanol (20 ml) was stirred with 10% palladium on carbon (50 mg) under 1 atmosphere of hydrogen for 16 hours at room temperature. The mixture was filtered through Celite® (diatomaceous earth, Johns-Manville, New York, N.Y.), and evaporated to dryness to give 5'-amino-5'-deoxy-2',3'-O-(1-methylethylidene)-6-N-phenyl adenosine (414 mg) as a colorless foam.

To a room temperature solution of 5'-amino-5'-deoxy-2',3'-O-(1-methylethylidene)-6-N-phenyl adenosine (414 mg) in dry dichloromethane (15 ml) was added triethylamine (0.5 ml) and a solution of sulfamoyl chloride (1.05M in acetonitrile, 1.2 ml). After 4 hours additional sulfamoyl chloride (1.05M in acetonitrile, 1.0 ml) was added and the mixture was left for 2 days at room temperature. The mixture was then poured into dichloromethane (100 ml), washed with water (2×50 ml), dried over anhydrous magnesium sulfate and evaporated. The residue was then purified by silica gel chromatography (60–100% ethylacetate in hexanes) to give 5'-deoxy-2',3'-O-(1-methylethylidene)-6-N-phenyl-adenosine 5'-N-sulfamide (140 mg) as a colorless foam.

To a room temperature solution of 5'-deoxy-2',3'-O-(1-methylethylidene)-6-N-phenyl-adenosine 5'-N-sulfamide (140 mg) in dry dichloromethane (5 ml) was added triethylamine (170 μl), 4-dimethylaminopyridine (19 mg), N-tert butoxycarbonyl-L-phenylalanine (97 mg) and ethyl-3-(3-dimethylaminopropyl)carbodiimide hydrochloride (88 mg). The mixture was stirred under an atmosphere of nitrogen for 1 day before ethyl-3-(3-dimethylaminopropyl)carbodiimide hydrochloride and (100 mg) and N-tert butoxycarbonyl-L-phenylalanine (100 mg) were added. After 1 day the mixture was poured into dichloromethane (50 ml) washed with water (25 ml) dried over anhydrous magnesium sulfate and evaporated to yield a colorless oil. Purification by silica gel chromatography (2% methanol in dichloromethane) gave 5'-deoxy-2',3'-O-(1-methylethylidene)-6-N-phenyl-adenosine 5'-N-(N-tertbutoxycarbonyl-L-phenylalanyl)sulfamide (101 mg) as a white solid.

5'-deoxy-2',3'-O-(1-methylethylidene)-6-N-phenyl-adenosine 5'-N-(N-tertbutoxycarbonyl-L-phenylalanyl)sulfamide (32 mg) was stirred at room temperature in trifluoroacetic acid /water (5:2. 1.5 ml) for 2 hours before being evaporated to dryness to give 5'-deoxy-6-N-phenyl-adenosine 5'-N-(N-L-phenylalanyl)sulfamide (34 mg) as a white solid.

Example 2

Preparation of 5'-deoxy-adenosine 5'-N-(N-L-phenylalanyl)sulfamide (CB 16913)

To a stirred 0° C. solution of chlorosulfonylisocyanate (5.33 mL) in dichlomethane (100 ml), was added dropwise benzyl alcohol (6.34 ml), and the mixture was stirred at 0° C. for 1 h. The solvent was evaporated and the resulting white colored residue was redissolved in dichloromethane (100 ml), and added via cannula to an ice-cold solution of 5'-amino-5'-deoxy-adenosine (17.07 g) and triethylamine (40 ml) in dichloromethane (500 ml). The resulting reaction mixture was allowed to warm to room temperature overnight. After 14 h, an additional amount of N-benzyloxycarbonylsulfamoyl chloride (2.5 g) was added. After an additional 24 h the mixture was washed with water (200 ml) and dried over anhydrous sodium sulfate. Evaporation of the solvent gave 5'-deoxy-2',3'-O-(1-methylethylidene)-adenosine 5'-N-[(phenylmethoxy)carbonyl]-sulfamide as an off white colored solid (39.5 g).

Ten percent Pd-C (5.5 g) was added to 5'-deoxy-2',3'-O-(1-methylethylidene)-adenosine 5'-N-[(phenylmethoxy)carbonyl]sulfamide (39.5 g) under a nitrogen atmosphere, followed by addition of 95% ethanol (30 ml) and methanol (1 L). The mixture was stirred under hydrogen at 1 atmosphere for 24 h. An additional amount of 10% Pd-C (5.0 g) was added and after 30 h the catalyst was removed by filtration. Evaporation of the solvent gave 5'-deoxy-2',3'-O-(1-methylethylidene)-adenosine 5'-N-sulfamide (20.7 g) as a white solid.

To a stirred solution of N-tertbutoxycarbonyl-L-phenylalanine (2.97 g) in anhydrous acetonitrile (100 ml) was added carbonyldiimidazole (2.18 g) the mixture was stirred at room temperature for 30 min, then added via cannula to a stirred suspension of 5'-deoxy-2',3'-O-(1-methylethylidene)-adenosine 5'-N-sulfamide (4.31 g) and diazabicycloundecene (1.92 ml) in anhydrous acetonitrile (80 mL). After 16 h at room temperature an additional amount of active ester of N-tertbutoxycarbonyl-L-phenylalanine (55.6 mmol) (freshly prepared as above) and diazabicycloundecene (0.96 ml) were added and the mixture was stirred for 6 h. Evaporation gave a residue that was purified by silica gel chromatography (5 % methanol in dichloromethane) to give 5'-deoxy-2',3'-O-(1-methylethylidene)-adenosine 5'-N-(N-tertbutoxycarbonyl-L-phenylalanyl)sulfamide as a white solid (3.23 g).

Twelve percent HCl in ethyl acetate (80 ml) was added dropwise to a 0° C. solution of 5'-deoxy-2',3'-O-(1-methylethylidene)-adenosine 5'-N-(N-tertbutoxycarbonyl-L-phenylalanyl)sulfamide (1.9 g) in anhydrous ethyl acetate (100 ml). After 5 h the solvent was evaporated to give a white residue. To the residue was added trifluoroacetic acid (15 ml) and water (6 ml), the resulting mixture was stirred for 1 h at room temperature. The solvent was coevaporated with toluene (3×30 ml) and the residue triturated with anhydrous ether to give 5'-deoxy-adenosine 5'-N-(N-L-phenylalanyl)sulfamide as a white solid (1.4 g).

Example 3

Preparation of 5'-deoxy-adenosine 5'-N-(N-L-tryptophanyl)sulfamide

To a stirred solution of N-tertbutoxycarbonyl-L-tryptophan (400 mg) in anhydrous acetonitrile (10 ml) was added carbonyldiimidazole (250 mg). The mixture was stirred at room temperature for 1 hour then added, via cannula, to a stirred suspension of 5'-deoxy-2',3'-O-(1-methylethylidene)-adenosine 5'-N-sulfamide (510 mg) and diazabicycloundecene (0.22 mL) in anhydrous acetonitrile (14 ml). After 3 days the mixture was evaporated to dryness and the residue was purified by silica gel chromatography (1% acetic acid in 5% methanol in dichloromethane) to give 5'-deoxy-2',3'-O-(1-methylethylidene)-adenosine 5'-N-(N-tertbutoxycarbonyl-L-tryptophanyl)sulfamide as a colorless foam (550 mg).

5'-deoxy-2',3'-O-(1-methylethylidene)-adenosine 5'-N-(N-tertbutoxycarbonyl-L-tryptophanyl)sulfamide (550 mg) was stirred at room temperature in trifluoroacetic acid (5 ml) and water (2 ml) for 2 hours before being evaporated to dryness. The residue was washed with diethylether (3×10 ml) and dried to yield 5'-deoxy-adenosine 5'-N-(N-L-tryptophanyl)sulfamide (538 mg) as a white powder.

Example 4

Preparation of 5'-deoxy-adenosine 5'-N-(N-L-seryl)sulfamide

To a stirred solution of N-carbobenzyloxy-O-benzyl-L-serine (544 mg) in anhydrous acetonitrile (10 mL) was added carbonyldiimidazole (267 mg). The mixture was stirred at room temperature for 1 hour then added, via cannula, to a stirred suspension of 5'-deoxy-2',3'-O-(1-methylethylidene)-adenosine 5'-N-sulfamide (530 mg) and diazabicycloundecene (206 µl) in anhydrous acetonitrile (15 mL). After 1 day methanol (5 ml) was added and the mixture was evaporated to dryness. The residue was purified by silica gel chromatography (1% acetic acid in 5% methanol in dichloromethane) to give 5'-deoxy-2',3'-O-(1-methylethylidene)-adenosine 5'-N-(N-carbobenzyloxy-O-benzyl-L-seryl)-sulfamide as a colorless foam (411 mg).

To a stirred solution of 5'-deoxy-2',3'-O-(1-methylethylidene)-adenosine 5'-N-(N-carbobenzyloxy-O-benzyl-L-seryl)sulfamide (411 mg) in methanol (25 ml) was added 10% palladium on carbon (250 mg) and formic acid (1 ml). The mixture was stirred at room temperature for 1 day before being filtered through Celite® (diatomaceous earth, Johns-Manville, New York, N.Y.), and evaporated to dryness, leaving 5'-deoxy-adenosine 5'-N-(N-L-seryl)sulfamide (102 mg) as a pale cream powder.

BIOLOGICAL EVALUATION $IC_{50}$ determinations for the aminoacyl-tRNA synthetases (aaRS) isolated from HeLa cells were carried out using a modification of the aaRS charging and trichloroacetic acid precipitation assay described previously (see examples: D. Kern et. al., Biochemie, 61, 1257–1272 (1979) and J. Gilbart et. al. Antimicrobial Agents and Chemotherapy, 37(1), 32–38 (1993)). The aaRS enzymes were partially purified from extracts of HeLa cells and the activity of each aaRS enzyme standardized as trichloroacetic acid precipitable counts (cpm) obtained at 10 minutes reaction time at Km concentrations of substrates. For practical purposes, the minimal acceptable value is approximately 2000 cpm per 10 minute reaction. The final dilution of the HeLa extract in the assays for the aaRS enzymes varies from 50 to 1200-fold.

Preincubations for $IC_{50}$ determinations were begun by incubating HeLa aaRS extracts in 50 mM HEPES (pH 7.5), 0.1 mM EDTA, 0.05 mg/ml bovine serum albumin, 10 mM dithiothreitol and 2.5% dimethyl sulfoxide with and without test compound in a final volume of 20 microliters in a microtiter plate for 20 minutes at 25° C. Test compounds were typically present as serial dilutions in concentrations ranging from 0.35 nM to 35 μM. Test compound solutions were prepared by dissolving test compounds in 100% dimethyl sulfoxide and diluting to the final concentration with 50 mM HEPES, pH 7.5. $IC_{50}$ determinations were typically performed in duplicate with each experiment containing 4–8 concentrations of test compound and with duplicate controls containing no inhibitor.

$IC_{50}$ incubations were initiated by supplementing the preincubation mixture to a final assay concentration of 10 mM $MgCl_2$, 30 mM KCl, 10 mM KFl, 50 mM HEPES (pH 7.5), 20–500 mM ATP, 2–20 μM [$^3$H] amino acid, and 90–180 μM crude brewers yeast tRNA in a final volume of 35 microliters. The reaction was incubated at 25° C. for 5–20 minutes. At specified time points a 15 microliter aliquot was removed and added to a well of a Millipore filtration plate (Multiscreen-FB, MAFB NOB 10) containing 100 microliters of cold 5% (wt/vol) trichloroacetic acid. Trichloroacitic acid precipitable material was collected by filtration on a Millipore Multiscreen filtration station, washed twice with cold 5% trichloroacetic acid, twice with water, and dried. Plates were typically allowed to air dry for several hours or baked at 50° C. in a vacuum oven for 30 minutes. The radioactivity on the dried plates was quantitated by the addition of Packard Microscint-20 to the wells and counting with a Packard TopCount scintillation counter.

Inhibitor activity typically was reported as a percentage of the control aaRS activity. The $IC_{50}$ value was determined by plotting per cent activity versus compound concentration in the assay and identifying the concentration at which 50% of the activity was remaining. The $IC_{50}$ (in nM, Hela Cells) values of representative compounds of the present invention are listed in column 5 of Table I.

TABLE I

| Compound Number | Structure | Mass Spectrum | HPLC* retention time (%) Acetonitrile | $IC_{50}$ (nM) in HeLa Cells | General Procedure |
|---|---|---|---|---|---|
| I | 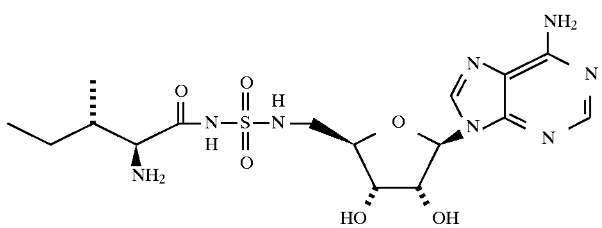 | Calc for M + H 459.1774 Obtained 459.1761 | 10.43 min (5%) | 0.9 | 1 |
| II | 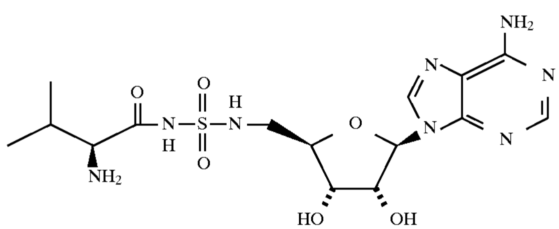 | Calc for M + H 445.1618 Obtained 445.1609 | 4.77 min (5%) | 27.0 | 1 |
| III | 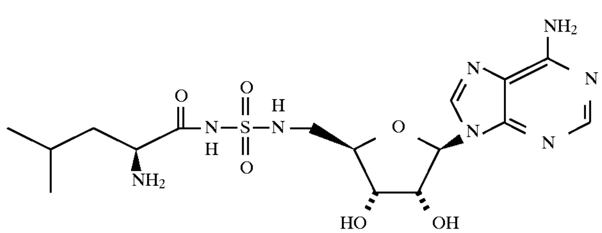 | Calc for M + H 459.1774 Obtained 459.1762 | 10.53 min (5%) | 0.5 | 1 |
| IV | 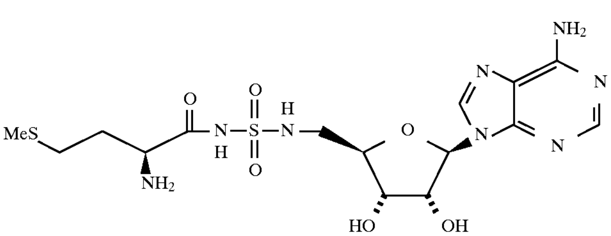 | Calc for M + H 477.1338 Obtained 477.1350 | 6.67 min (5%) | 3.0 | 1 |

TABLE I-continued

| Compound Number | Structure | Mass Spectrum | HPLC* retention time (%) Acetonitrile | IC$_{50}$ (nM) in HeLa Cells | General Procedure |
|---|---|---|---|---|---|
| V | (Tyrosine-sulfamoyl-adenosine structure) | Calc for M + H 509.1567 Obtained 509.1552 | 6.03 min (5%) | 17.0 | 1 |
| VI | (Serine-sulfamoyl-adenosine structure) | Calc for M + H 433.1254 Obtained 433.1246 | 2.07 min (5%) | 140.0 | 1 |
| VII | (Alanine-sulfamoyl-adenosine structure) | Calc for M + Cs 549.0281 Obtained 549.0267 | 2.21 min (5%) | 22.0 | 1 |
| VIII | (Aspartate-sulfamoyl-adenosine structure) | Calc for M + H 461.1203 Obtained 461.1218 | 1.89 min (5%) | 174.0 | 1 |
| IX | (Glycine-sulfamoyl-adenosine structure) | Calc for M + H 535.0124 Obtained 535.0119 | 2.04 min (5%) | 50.0 | 1 |
| X | (Tryptophan-sulfamoyl-adenosine structure) | Calc for M + H 664.0703 Obtained 664.0719 | 5.03 min (10%) | 300.0 | 1 |

TABLE I-continued

| Compound Number | Structure | Mass Spectrum | HPLC* retention time (%) Acetonitrile | IC$_{50}$ (nM) in HeLa Cells | General Procedure |
|---|---|---|---|---|---|
| XI | 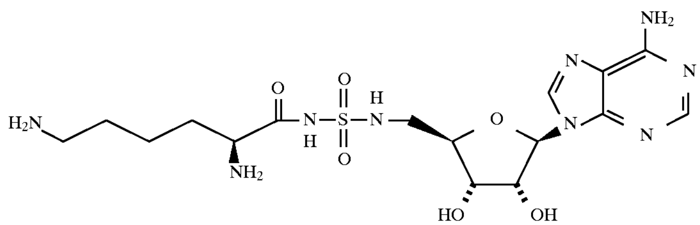 | Calc for M + H 474.1883 Obtained 474.1894 | 2.39 min (2%) | 8.0 | 1 |
| XII | 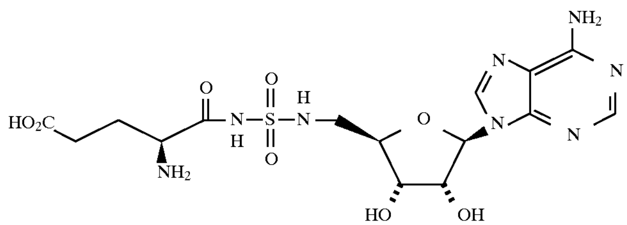 | Calc for M + H 475.1360 Obtained 475.1372 | 1.89 min (5%) | NA | 1 |
| XIII | 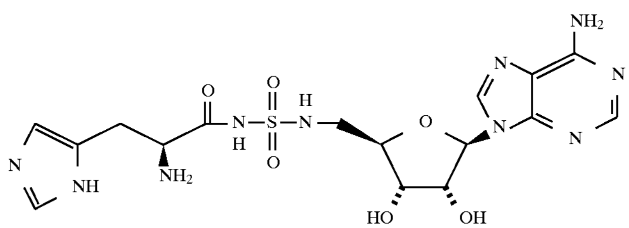 | Calc for M + H 615.0499 Obtained 6155.0526 | 2.25 min (5%) | 2.0 | 1 |
| XIV | 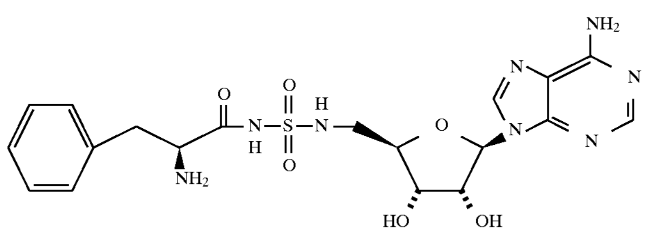 | Calc for M + H 493.1618 Obtained 493.1609 | 3.62 min (10%) | 5.0 | 1 |
| XV | 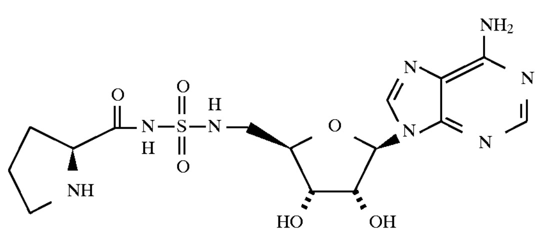 | Calc for M + H 443.1461 Obtained 443.1453 | 2.75 min (5%) | 1.0 | 1 |
| XVI | 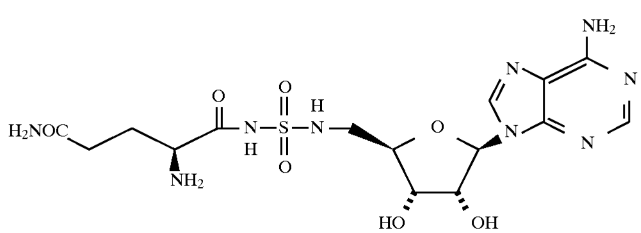 | Calc for M + H 474.1519 Obtained 474.1529 | 2.88 min (5%) | 400.0 | 1 |

TABLE I-continued

| Compound Number | Structure | Mass Spectrum | HPLC* retention time (%) Acetonitrile | IC$_{50}$ (nM) in HeLa Cells | General Procedure |
|---|---|---|---|---|---|
| XVII | 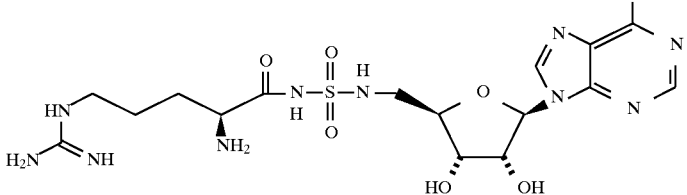 | Calc for M + H 502.1945 Obtained 502.1960 | 2.04 min (5%) | 14.0 | 1 |
| XVIII | 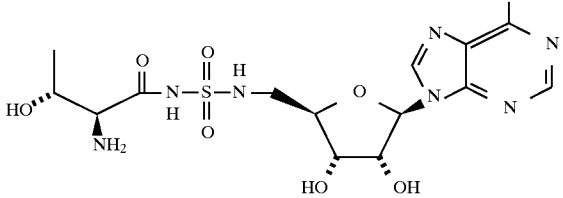 | Calc for M + H 447.1410 Obtained 447.1421 | 2.33 min (5%) | 40.0 | 1 |
| XIX | 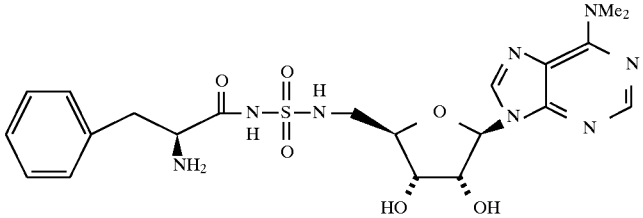 | Calc for M + H 521.1941 Obtained 521.1942 | 4.61 min (16%)[a] | | 2 |
| XX | 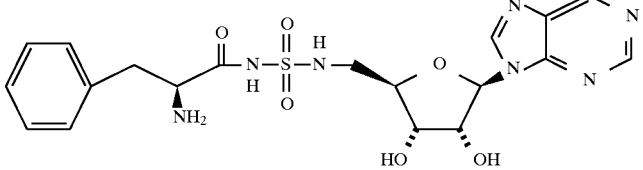 | Calc for M + H 569.21 Obtained 569.88 | 4.48 min (28%) | | 2 |

Me = methyl; Ph = phenyl
*(%) Acetonitrile/10 mM KH$_2$PO$_4$, pH 7.0, detection: 254 nM, flow rate: 1.2 ml/min., column: Inertsil ® C-8 (Metachem Technology Inc., Torrance, CA), 4.6 mm × 150 mm + precolumn.
[a]column: inertsil ® C-4 (Metachem Technology Inc., Torrance, CA) under above conditions.

MTT Assay

The MTT assay was used as a model to measure the inhibitory effects of the compounds of Formula I. The MTT assay is considered the most convenient modern assay for the determination of cell viability and cell proliferation. An MTT assay kit is commercially available (Chemicon International Inc., Temecula, Calif.). The MTT assay was performed according to manufacturer's instructions as outlined below.

A human epidermoid carcinoma cell line, designated as A-253 (ATCC HTB 41), was obtained in frozen vials from the American Type Culture Collection, Rockville, Md. Monolayer cultures were established from the vials by growth in RPMI 1640 medium supplemented with 10% fetal bovine serum (heat-inactivated), 2 mM L-glutamine, and pen-strep (100 units/ml; 100 µg/ml). The cultures were incubated at 37±1.5° C. in 5±1% CO$_2$ in humidified air and were passaged weekly to avoid overgrowth. The laboratory cultures used for the present study were at passage seven after receipt of frozen stocks from ATCC.

Compounds of Formula I in powder form were stored at room temperature in plastic micro centrifuge tubes. Each tube was placed in a plastic bag containing desiccant. Each test compound was prepared as a 2 mg/ml solution in RPMI 1640 medium (non-supplemented) on the day of use, and the appropriate dilutions were prepared with the same vehicle.

Each compound was handled by sterile techniques in Class II, Type B biological safety cabinets.

The reference control compound was methotrexate at concentrations of 0.5 µg/ml to 50 µg/ml. A 1 mg/ml stock was prepared on the day of dosing and diluted to the appropriate concentrations using RPMI 1640 medium (non-supplemented).

A blank control was included in the MTT assay in order to determine the absorbance associated with the absence of any cells. This control was RPMI 1640 culture medium carried through the same procedures used to culture the cells in the microwell plates and to conduct the MTT assay color development. The microwell plate reader was zeroed against the blank control prior to recording the absorbance in the test wells.

Laboratory monolayer cultures of A-253 cells were trypsinized and seeded at a concentration of 24,000 cells in 0.05 ml of complete RPMI 1640 culture medium per well in 96-well plates. Eight wells in a column were seeded for each test condition. The blank control was prepared by adding 0.05 ml of culture medium (no cells) to 8 wells in the first column of each plate. A separate microwell plate was used for each compound of Formula I.

The test compound treatments were initiated immediately after seeding the cells by adding 0.05 ml of treatment medium to each microwell. Ten different test compound concentrations were prepared in culture medium (without serum), and each concentration was applied to a volume of eight wells on the appropriate plate. The final concentrations in the wells were 1000, 500, 250, 100, 50, 25, 10, 5, 2.5, and 1 µg/ml.

An untreated (zero-dose) condition was included as a column of 8 wells on each plate. The zero-dose and blank control wells received 0.05 ml of culture medium (without serum). The microwell plates were placed in an incubator at $37\pm1.5°$ C. in 5% $CO_2$ in humidified air for an exposure period of $72\pm0.5$ hours.

After the exposure period, 0.1 ml of MTT dye solution (0.5 mg/ml in serum free RPMI 1640 medium) was added to each micowell. The cultures were returned to the incubator for $2\pm0.1$ hours. Then the medium was removed from each well and placed into a clean microwell plate for temporary storage. A volume of 0.1 ml of color development solution (Solution C, isopropanol with 0.04M HCl, Chemicon MTT Assay kit, Chemicon International Inc., Temecula, Calif.) was added to each new microwell. The contents were carefully mixed and allowed to sit at room temperature for approximately 1 hour. The medium that was saved from each microwell then was pipetted back into the well from which it originally came. The absorbance at 540 nm wavelength was determined in a microwell plate reader within two hours of the final preparation of the plates.

The absorbance at 540 nm was recorded for each well by the microwell plate reader after the instrument was zeroed against the blank controls for each plate. The mean absorbance for each test condition was calculated and compared to the mean absorbance for the zero-dose wells in order to obtain percent values. The percent values provided a measure of the reduction in cell number as a result of the treatment with each concentration of test compound.

The percent zero-dose values for each concentration of test compounds were plotted against the logarithm of the dose. The plotting was performed by SigmaPlot® (Statistical Products Sevice Solutions Inc., Chicago, Ill.) scientific graphing software, and the points were fitted by a third order regression curve. Where the curve crossed the 50% line for reduction in absorbance from the zero-dose, a vertical line was dropped to the concentration axis to determine the $IC_{50}$ value, the concentration of a compound of Formula I that reduced the cell number by 50%. For test compounds that were active at the lowest applied dose, the plot was extended in a reasonable manner by eye in order to estimate the $IC_{50}$ value. The $IC_{50}$ values determined from the MTT assay are summarized in column 2 of Table II.

TABLE II $IC_{50}$ Values in MTT Assays

| Compound Number | $IC_{50}$ (µM) Human Epidermoid Carcinoma Cells ATCC # HTB 41 | $IC_{50}$ (µM) Normal Skin Fibroblast ATCC # CRL 1501 |
| --- | --- | --- |
| I | 3.05 | |
| II | 4.95 | |
| III | 1.37 | 13.0 |
| IV | 1.05 | |
| V | 0.79 | |
| VI | 9.25 | |
| VII | 1.44 | |
| VIII | 5.00 | |
| IX | 1.49 | |
| X | 0.53 | 0.08 |
| XI | 2.53 | |
| XII | 10.54 | |
| XIII | 2.69 | |
| XIV | 0.53 | 5.58 |
| XV | 0.90 | |
| XVI | 3.59 | |
| XVII | 3.99 | |
| XVIII | 9.63 | |
| Methotrexate | 0.04 | |
| Retinoic acid | 266.31 | |

The MTT assay was conducted in a similar manner on normal human skin fibroblasts cell line ATCC CRL 1501. The results of this assay are summarized in Column 3 in Table II.

Skin Penetration Study

Five formulations of Compound XIV were prepared for in vitro study. The formulations are represented in Table III

TABLE III

Formulation of Compound XIV for in vitro Skin Penetration Study

| | % W/W | | | | |
| --- | --- | --- | --- | --- | --- |
| Components | Oil in Water Cream CU-12A | Aqueous Gel CU-6A | Anhydrous Ointment CU-11A | Anhydrous Ointment CU-10A | Anhydrous Ointment CU-13A |
| Compound XIV | 0.05 | 0.05 | 0.05 | 0.05 | 0.05 |
| White Petrolatum, USP | 10 | — | — | — | — |
| Stearyl Alcohol, NF | 5 | — | — | — | — |
| Catyl Alcohol, NF | 0.5 | — | — | — | — |
| Light Mineral Oil, NF | 5 | — | — | — | — |
| Brill 72 | 2 | — | — | — | — |
| Brill 721 | 2 | — | — | — | — |
| Propylene Glycol, USP | 10 | 10 | 10 | 4.0 | — |
| Hydroxyethyl Cellulose, NF | 0.3 | — | — | — | — |

TABLE III-continued

Formulation of Compound XIV for in vitro Skin Penetration Study

| | % W/W | | | | |
|---|---|---|---|---|---|
| Components | Oil in Water Cream CU-12A | Aqueous Gel CU-6A | Anhydrous Ointment CU-11A | Anhydrous Ointment CU-10A | Anhydrous Ointment CU-13A |
| Methylparaben, NF | 0.2 | 0.2 | — | — | — |
| Propylparaben, NF | 0.05 | 0.04 | — | — | — |
| Potassium Hydroxide, USP (10% aq.) | — | QS pH 8 | — | — | — |
| Carbomer 98O, NF | — | 1.25 | — | — | — |
| Polyethylene Glycol 3350, NF | — | — | 35 | — | — |
| Polyethylene Glycol 400, NF | — | — | QSAD 100 | — | — |
| White Wax, NF | — | — | — | 5.0 | 5.0 |
| Glycol Monostearate | — | — | — | 2.0 | 2.0 |
| Cholesterol, NF | — | — | — | 1.0 | 1.0 |
| Glycerin, USP | — | — | — | — | 8.0 |
| 50 mM Sodium Phosphate Buffer pH 7 | 5 | — | — | — | — |
| White Petrolatum USP | — | — | — | QSAD 100 | QSAD 100 |
| Pure Water | QSAD 100 | QSAD 100 | — | — | — |

Franz static diffusion chambers were filled with a 4% BSA isotonic buffered saline and equilibrated to a temperature of 37° C. by a circulating water pump. Excised human cadaver skin (~0.2 mm thickness), which is either intact or tape-stripped, is placed onto each chamber.

The test formulations containing non-radioactive Compound XIV were spiked with tritiated Compound XIV. The specific radioactivity was about 0.05 $\mu$Ci/mg test formulation. Spiked formulations were applied to the skin surface. The specific radioactivity in the stratum corneum, epidermis, dermis and the reservoir were measured at 1, 3, 6 and 24 h time points by liquid scintillation counting, to investigate cumulative penetration at each time point. The specific activity is expressed as a percentage relative to the total recovery from the reservoir, skin wipes, and the respective skin layers at the end of each experiment.

Each of the five formulations were tested on intact skin (5 replicates each) and tape-stripped skin (only in one diffusion cell) to investigate cumulative penetration at 0, 1, 3, 6, and 24 hours and tissue recovery was measured at 24 hours.

In addition, four of the formulations were again tested in intact skin (5 replicates each) and tape-stripped skin (only in one diffusion cell) to investigate cumulative penetration at 0, 1, 3, and 6 hours and tissue recovery was measured at 6 hours. The transdermal absorption of Compound XIV through intact human cadaver skin is expressed in Table IV. The localization of Compound XIV in human cadaver skin is expressed in Table V.

The results indicate that Compound XIV penetrates the target tissue, epidermis, in significant concentration at 6 hours and levels are generally increased at 24 hours. These results are indicative of the usefullness of the compounds of the present invention for topical treatment of hyperproliferative disorders.

TABLE IV

Transdermal Absorption of Compound XIV through Intact Human Cadaver Skin (% of Applied Dose In Reservoir)

| Formulation | 0 hour | 1 hour | 3 hour | 6 hour | 24 hour |
|---|---|---|---|---|---|
| CU-6A, 6 hr | 0.00 ± 0.00 | 0.09 ± 0.02 | 0.29 ± 0.06 | 0.48 ± 0.08 | |
| CU-6A, 24 hr* | 0.00 ± 0.00 | 0.09 ± 0.02 | 0.28 ± 0.03 | 0.41 ± 0.06 | 0.49 ± 0.03 |
| CU-10A, 6 hr* | 0.00 ± 0.00 | 0.10 ± 0.02 | 0.32 ± 0.06 | 0.42 ± 0.03 | |
| CU-10A, 24 hr | 0.00 ± 0.00 | 0.14 ± 0.04 | 0.28 ± 0.05 | 0.32 ± 0.05 | 0.59 ± 0.05 |
| CU-11A, 6 hr | 0.00 ± 0.00 | 0.004 ± 0.002 | 0.023 ± 0.004 | 0.043 ± 0.013 | |
| CU-11A, 24 hr | 0.00 ± 0.00 | 0.005 ± 0.003 | 0.019 ± 0.005 | 0.035 ± 0.010 | 0.095 ± 0.023 |
| CU-12A, 6 hr | 0.00 ± 0.00 | 0.18 ± 0.03 | 0.22 ± 0.04 | 0.37 ± 0.09 | |
| CU-12A, 24 hr | 0.00 ± 0.00 | 0.14 ± 0.04 | 0.22 ± 0.05 | 0.32 ± 0.04 | 1.00 ± 0.14 |
| CU-13A, 24 hr* | 0.00 ± 0.00 | 0.04 ± 0.01 | 0.09 ± 0.00 | 0.16 ± 0.02 | 0.54 ± 0.11 | n = 5; *: n = 4

TABLE V

Localization of Compound XIV in Human Cadaver Skin (% of Applied Dose In Reservoir)

| Formulation | Reser | Dermis | Epi | Str. | SC | Gauze | 2X | Total |
|---|---|---|---|---|---|---|---|---|
| CU-6A, 6 hr | 0.48 ± 0.08 | 0.11 ± 0.08 | 0.6 ± 0.41 | 0.69 ± 0.16 | 0.3 ± 0.2 | 1.8 ± 0.8 | 94.7 ± 5.0 | 98.7 ± 6.7 |
| CU-6A, 24 hr* | 0.49 ± 0.03 | 0.03 ± 0.01 | 0.57 ± 0.28 | 0.49 ± 0.19 | 0.2 ± 0.1 | 0.5 ± 0.2 | 85.3 ± 11.7 | 87.6 ± 12.5 |
| CU-10A, 6 hr* | 0.42 ± 0.03 | 0.10 ± 0.04 | 0.75 ± 0.56 | 1.24 ± 0.33 | 0.4 ± 0.2 | 26.7 ± 6.1 | 62.2 ± 7.6 | 91.8 ± 14.8 |
| CU-10A, 24 hr | 0.59 ± 0.05 | 0.15 ± 0.08 | 1.32 ± 0.39 | 1.96 ± 0.53 | 1.0 ± 0.8 | 30.4 ± 8.1 | 60.9 ± 7.6 | 96.3 ± 17.4 |
| CU-11A, 6 hr | 0.04 ± 0.01 | 0.02 ± 0.01 | 0.08 ± 0.01 | 0.12 ± 0.05 | 0.1 ± 0.0 | 0.3 ± 0.1 | 77.2 ± 14.9 | 77.8 ± 15.2 |
| CU-11A, 24 hr | 0.09 ± 0.02 | 0.03 ± 0.01 | 0.18 ± 0.05 | 0.14 ± 0.03 | 0.08 ± 0.02 | 0.51 ± 0.26 | 99.0 ± 13.4 | 100.1 ± 13.8 |
| CU-12A, 6 hr | 0.37 ± 0.09 | 0.03 ± 0.01 | 0.27 ± 0.10 | 0.53 ± 0.11 | 0.16 ± 0.03 | 0.65 ± 0.39 | 75.2 ± 4.5 | 77.2 ± 5.2 |
| CU-12A, 24 hr | 1.0 ± 0.14 | 0.07 ± 0.04 | 0.74 ± 0.26 | 0.50 ± 0.07 | 0.14 ± 0.04 | 1.28 ± 0.47 | 74.6 ± 3.6 | 78.3 ± 4.6 |
| CU-13A, 24 hr* | 0.54 ± 0.11 | 0.08 ± 0.04 | 2.20 ± 0.68 | 2.33 ± 0.76 | 1.30 ± 0.58 | 58.0 ± 33.5 | 10.0 ± 2.37 | 74.4 ± 38.0 | n = 5;
*: n = 4

The ability of the compounds of the present invention to penetrate the skin cells is surprising and unexpected in light of the difficulty reported in transporting structurally similar compounds across cell membranes. Osada et al. have reported (See H. Osada and K. Isono, *Antimicrobial Agents and Chemotherapy*, 27 (2) 230–233 (1985)) that ascamycin is an ineffective inhibitor against bacterial growth due to an interference of the alanyl side chain with membrane transport. Hill et al. have reported (see PCT patent application no. WO97/05132) that a variety of sulfamoyl aminoacyl adenylate analogs are effective inhibitors of aminoacyl tRNA synthetases and are able to penetrate whole cells. Applicants have prepared the sulfamidyl analogs for two of these aminoacyl adenylate mimics and have shown (unpublished) that, although the sulfamidyl analogs are effective inhibitors of aminoacyl tRNA synthetases, they are unable to penetrate whole cells. This inability to penetrate whole cells presumably is due to a problem with transport across cell membranes.

Acute Toxicity of Compound XIV in the Mouse

Six groups containing 5 CD-1 female mice (Charles River Lab, Mass.) weighing 19–23 g were used in the experiment. Water and Agway rodent chow were provided ad libitum throughout the study. The laboratory animals were handled according to the institutional animal husbandry Standard Operating Procedures.

Compound XIV (60 mg) was dissolved in 6.0 ml of sterile normal saline to give a solution of 10 mg/ml. The solution was filtered with 0.2 μm Nalgene syringe filter and then further diluted serially with normal saline by 5-fold (0.6 ml to 3.0 ml) to 0.016 mg/ml. Group 1 animals were injected intraperitoneally (i.p.) with 10 ml/kg normal saline as negative controls. Groups 2 to 6 were given Compound XIV i.p. at 100, 20, 4, 0.8 and 0.16 mg/kg, respectively.

All the animals were observed for mortality, body weight, general behavior and physiological state after dosing. The $LD_{50}$ of the compound was calculated by the Method of Probits (See Probit Analysis, 3rd Edition, D. J. Finney, Cambridge University Press, Cambridge, 1971). All surviving animals were sacrificed after the last observation on seventh day post-treatment.

The $LD_{50}$ of Compound XIV was determined as 44 mg/kg, intraperitoneally in the mice. The 95% confidence limit of the $LD_{50}$ was calculated as 24–63 mg/kg. The mice in group 2 (100 mg/kg) showed loose hair starting at 3–4 hours after dosing and they also lost their appetite and became less active. No other unusual symptoms were observed. Most of the group 2 mice died between 8 to 24 hours after injection. The mice in group 3 (20 mg/kg) lost about 10% of their body weight after injection, but there were no unusual symptoms observed. Mice dosed at 0.16 to 4 mg/kg ( groups 4–6) as well as the control group animals (group 1) appeared normal during the experiment. The study shows that a high dose of Compound XIV was tolerated.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A compound of the Formula:

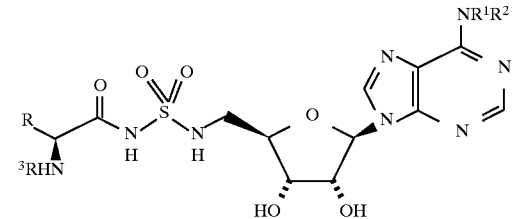

(a) wherein R is selected from the group consisting of hydrido, alkyl, cycloalkyl, aryl and arylalkyl;
(b) wherein each of $R^1$ and $R^2$ is independently selected from the group consisting of hydrido, alkyl, aryl and arylalkyl;
(c) wherein R and $R^3$ can together form a pyrrolidine ring, alternatively, $R^3$ is hydrido; and pharmaceutically-acceptable salts thereof.

2. The compound of claim 1 wherein (a) R is selected from the group consisting of hydrido, alkyl and arylalkyl; and (b) wherein each of $R^1$ and $R^2$ is hydrido.

3. The compound of claim 2 selected from the compounds, or a pharmaceutically-acceptable salt thereof, of the group consisting of 5'-deoxy-adenosine 5'-N(N-L-phenylalanyl)sulfamide and 5'-deoxy-adenosine 5'-N-(N-L-tryptophany)sulfamide.

4. A pharmaceutical composition comprising a therapeutically-effective amount of an active compound and a pharmaceutically-acceptable carrier, said active compound selected from a family of compounds of the Formula:

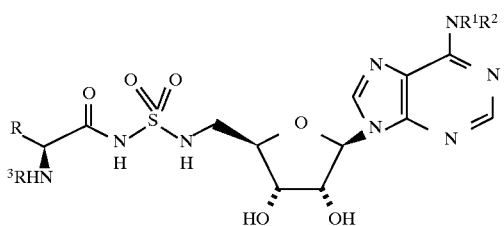

(a) wherein R is selected from the group consisting of hydrido, alkyl, cycloalkyl, aryl and arylalkyl;

(b) wherein each of $R^1$ and $R^2$ is independently selected from the group consisting of hydrido, alkyl, cycloalkyl, aryl and arylalkyl;

(c) wherein $R^1$ and $R^3$ can together form a proline, alternatively, $R^3$ is hydrido; and pharmaceutically-acceptable salts thereof.

5. The composition of claim 4 wherein the pharmaceutically-acceptable carrier is for topical administration.

6. The composition of claim 4 wherein (a) R is selected from the group consisting of hydrido, alkyl and arylalkyl; and (b) wherein each of $R^1$ and $R^2$ is hydrido.

7. The composition of claim 6 wherein said active compound is selected from the compounds, or a pharmaceutically-acceptable salt thereof, of the group consisting of 5'-deoxy-adenosine 5'-N(N-L-phenylalanyl)sulfamide and 5'-deoxy-adenosine 5'-N-(N-L-tryptophanyl)sulfamide.

8. A method of inhibiting an aminoacyl-tRNA synthetase comprising contacting said tRNA synthetase with a compound as claimed in any of claims 1–3.

9. A method of treating a mammal afflicted by or susceptible to a disease which is caused by a hyperproliferative disorder, said method comprising administering to the mammal a therapeutically-effective amount of the compound of the Formula:

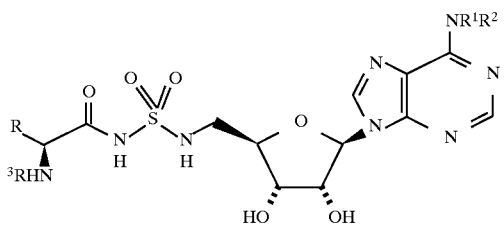

(a) wherein R is selected from the group consisting of hydrido, alkyl, cycloalkyl, aryl and arylalkyl;

(b) wherein each of $R^1$ and $R^2$ is independently selected from the group consisting of hydrido, alkyl, cycloalkyl, aryl and arylalkyl;

(c) wherein R and $R^3$ can together form a proline, alternatively, $R^3$ is hydrido; and pharmaceutically-acceptable salts thereof.

10. The method of claim 9 wherein the hyperproliferative disorder is psoriasis.

11. The method of claim 10 wherein the mammal is a human.

12. The method of claim 10 wherein (a) R is selected from the group consisting of hydrido, alkyl and arylalkyl; and (b) wherein each of $R^1$ and $R^2$ is hydrido.

13. The method of claim 12 wherein said compound is selected from the compounds, or a pharmaceutically-acceptable salt thereof, of the group consisting of 5'-deoxy-adenosine 5'-N(N-L-phenylalanyl)sulfamide and 5'-deoxy-adenosine 5'-N-(N-L-tryptophanyl)sulfamide.

14. A method of treating a mammal afflicted by or susceptible to psoriasis, said method comprising administering to the mammal a therapeutically-effective amount of a protein synthesis inhibitor.

15. The method of claim 14 wherein the protein synthesis inhibitor is a translational protein synthesis inhibitor.

16. The method of claim 15 wherein said protein synthesis inhibitor is a tRNA synthetase inhibitor.

17. The method of claim 16 wherein said tRNA synthetase inhibitor is a compound of the Formula:

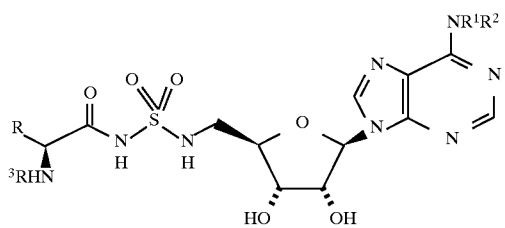

(a) wherein R is selected from the group consisting of hydrido, alkyl, cycloalkyl, aryl and arylalkyl;

(b) wherein each of $R^1$ and $R^2$ is independently selected from the group consisting of hydrido, alkyl, aryl and arylalkyl;

(c) wherein R and $R^3$ can together form a pyrrolidine ring, alternatively, $R^3$ is hydrido; and pharmaceutically-acceptable salts thereof.

18. The method of claim 17 wherein (a) R is selected from the group consisting of hydrido, alkyl and arylalkyl; and (b) wherein each of $R^1$ and $R^2$ is hydrido.

19. The method of claim 18 wherein said compound is selected from the compounds, or a pharmaceutically-acceptable salt thereof, of the group consisting of 5'-deoxy-adenosine 5'-N(N-L-phenylalanyl)sulfamide and 5'-deoxy-adenosine 5'-N-(N-L-tryptophanyl)sulfamide.

* * * * *